United States Patent [19]

Carney

[11] 3,960,874

[45] June 1, 1976

[54] 2-PHENOXY-ALKANOIC ACIDS

[75] Inventor: Richard William James Carney, New Providence, N.J.

[73] Assignee: Ciba-Geigy Corporation, Ardsley, N.Y.

[22] Filed: June 20, 1974

[21] Appl. No.: 481,281

Related U.S. Application Data

[63] Continuation-in-part of Ser. No. 336,668, Feb. 28, 1973, Pat. No. 3,895,032.

[52] U.S. Cl.................... 260/293.82; 260/239 BE;; 260/270 C; 260/293.83; 260/326.41
[51] Int. Cl.².......................................... C07D 295/14
[58] Field of Search................ 260/239 BE, 293.82, 260/293.83, 326.41, 270 C

[56] References Cited
UNITED STATES PATENTS 3,717,669  2/1973  Grant et al..................... 260/326.27

*Primary Examiner*—G. Thomas Todd
*Attorney, Agent, or Firm*—Joseph G. Kolodny; Theodore O. Groeger; John J. Maitner

[57] ABSTRACT

α-(Cyclic tert. aminophenoxy)-alkanoic acids, e.g., those of the formula

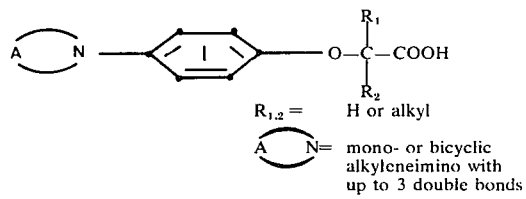

$R_{1,2}$ = H or alkyl
A–N = mono- or bicyclic alkyleneimino with up to 3 double bonds and functional derivatives thereof are anti-inflammatory and hypolipidemic agents.

8 Claims, No Drawings

2-PHENOXY-ALKANOIC ACIDS

CROSS-REFERENCE TO RELATED APPLICATION

This is a continuation-in-part of application Ser. No. 336,668, filed Feb. 28, 1973, now U.S. Pat. No. 3,895,032

SUMMARY OF THE INVENTION

The present invention concerns and has for its object the provision of new α-(cyclic tert. aminophenoxy)-alkanoic acids, preferably of those corresponding to Formula I

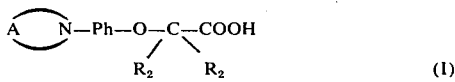

in which each of $R_1$ and $R_2$ is hydrogen or lower alkyl, Ph is unsubstituted phenylene or phenylene substituted by one or two members of the group consisting of lower alkyl, lower alkoxy, halogeno, trifluoromethyl or nitro and

is 5 to 7-ring-membered mono- or bicyclic lower alkyleneimino containing up to one double bond in the azacyclic ring and up to three double bonds in the carbocyclic bicyclic ring, which

is unsubstituted or substituted at the carbon atom adjacent to the imino nitrogen by one oxo group and, when aromatic, it is unsubstituted in the aromatic ring, or substituted as shown for Ph; or a lower alkyl ester, (lower alkoxy, di-lower alkylamino or lower alkyleneimino)-lower alkyl ester or a therapeutically useful ammonium, alkali metal, alkaline earth metal, aluminum or acid addition salt thereof, as well as of corresponding pharmaceutical compositions and of methods for the preparation and application of these products, which are useful anti-inflammatory and especially hypolipidemic agents in the treatment or management of arthritis and/or arteriosclerosis.

DESCRIPTION OF THE PREFERRED EMBODIMENTS

The lower alkyl radicals $R_1$ and $R_2$ represent, for example, methyl, ethyl, n- or i-propyl, -butyl, -pentyl, -hexyl or -heptyl. The term "lower," referred to above and hereinafter in connection with organic radicals or compounds respectively, defines such with up to 7, preferably up to 4, carbon atoms.

The phenylene radical Ph, carrying the tertiary amino group

in the 2-, preferably 3- or especially 4-position, is unsubstituted or substituted in the remaining positions by one or two, of the same or different substituents selected, for example, from lower alkyl, e.g., methyl, ethyl, n- or i-propyl or -butyl, lower alkoxy, e.g., methoxy, ethoxy, n- or i-propoxy or -butoxy, halogeno, e.g., fluoro, chloro, bromo or iodo; trifluoromethyl or nitro. More particularly, the phenylene radical Ph especially represents 1,3- or 1,4-phenylene, but also (lower alkyl)-1,3- or 1,4-phenylene, (lower alkoxy)-1,3- or 1,4-phenylene, mono- or di-(halogeno)-1,3- or 1,4-phenylene, (trifluoromethyl)-1,3- or 1,4-phenylene or (nitro)-1,3- or 1,4-phenylene.

The cyclic tertiary amino group

is preferably a monocyclic, 5 to 7 ring-membered lower alkyleneimino or especially a lower 2- or 3-alkenyleneimino group, but also 5 or 6 ring-membered bicyclic lower alkyleneimino or alkenyleneimino group, which latter contains 1–3 double bonds in the ring not containing the imino-nitrogen, e.g., pyrrolidino, piperidino, 1,4-, 1,5-, 1,6- or 2,5-hexyleneimino; 3-pyrrolino, 3-piperideino, 1,4-pent-2-enyleneimino, 2,5- or 1.6-enyleneimino; 4,5,6,7-tetrahydroindolino or -isoindolino, 1,2,3,4,5,6,7,8-octahydro-, 1,2,3,4,5,8,-hexahydro- or 1,2,3,4-tetrahydroquinolino or -isoquinolino. Said cyclic tert. amino group is either unsubstituted at any $CH_2$ ring-portion adjacent to the imino nitrogen, or substituted by one oxo group, thus transforming said portion to a CO group. Moreover, any aromatic ring in said bicyclic alkenyleneimino group is either unsubstituted or substituted as shown for the phenylene moiety Ph above.

Preferred esters and salts of the acids of Formula I are their lower alkyl, e.g., methyl, ethyl, n- or i-propyl or -butyl esters. Also valuable are the (lower alkoxy, di-lower alkylamino or lower alkyleneimino)-lower alkyl esters, wherein the oxygen or nitrogen atoms are separated from the carboxy-oxygen by at least 2 carbon atoms, e.g., the 2- or 3-(methoxy, ethoxy, dimethylamino, diethylamino, pyrrolidino or piperidino)-ethyl or -propyl esters respectively. Salts of said amphoteric acids are either the ammonium, alkali metal, alkaline earth metal or aluminum salts, e.g., the sodium, potassium, magnesium or calcium salts, or acid addition salts, advantageously derived from the therapeutically acceptable acids listed below.

The compounds of the invention possess valuable pharmacological properties. Besides anti-inflammatory activity, they exhibit primarily hypocholesterolemic and hypolipidemic, especially hypotriglyceridemic, effects, as is demonstrable in animal tests, using advantageously mammals, e.g., rats or dogs, as test objects. The compounds of the invention are administered to said mammals either enterally or parenterally, advantageously orally, but also introveneously, for example by intubation of aqueous or polyethyleneglycol 400 solutions or starchy suspensions to male rats, or by gelatine capsules, containing pure drug substances or a starchy suspension thereof, to male Beagle dogs. The dosage to be applied ranges between about 0.1 and 100 mg/kg/day, preferably between about 1 and 50 mg/kg/day, especially between about 3 and 30 mg/kg/day. Anti-inflammatory effects are advantageously estimated by the carrageenin rat-paw-edema test, according to which one hour after oral administration of the compounds of the invention, e.g., at the 50 mg/kg dosage level, 0.1 ml of a 1% aqueous saline suspension of carrageenin is injected into the plan tar area of one hind paw. Three to 4 hours later the difference of swelling is measured between contralateral and injected paw by means of mercury displacement, and compared with that obtained from control animals receiving the aqueous or starchy vehicle alone. Hypocholesterolemic and hypolipidemic activity is estimated in rats or dogs after daily administration of said compounds, e.g., with 50 mg/kg, and estimating at the 8 day total serum cholesterol and glycerides in orbital blood via an autoanalyser. In the fructose hypertriglyceridemic screen rats are intubated with said compounds, e.g., with 50 mg/kg for 3 days, after which treatment the animals are provided with 10% aqueous fructose ad libitum for 24 hours. Thereupon triglyceride and cholesterol levels in orbital blood are again provided by the autoanalyser. In view of the test results obtained, the compounds of the invention are useful anti-inflammatory and especially hypocholesterolemic and hypolipidemic agents, for example, useful in the treatment or management of arthritis and/or arteriosclerosis. Moreover, they are useful intermediates in the preparation of other valuable products, preferably of pharmacologically active agents.

Preferred anti-inflammatory, hypocholesterolemic and hypolipidemic compounds of the invention are those of Formula I, wherein:

a. $R_1$ is hydrogen, $R_2$ is hydrogen or lower alkyl, Ph is 1,3- or 1,4-phenylene, (lower alkyl)-1,3- or 1,4-phenylene, (lower alkoxy)-1,3- or 1,4-phenylene, mono- or di-(halogeno)-1,3- or 1,4-phenylene, (trifluoromethyl)-1,3- or 1,4-phenylene or (nitro)-1,3- or 1,4-phenylene and

is 5 to 7 ring-membered monocyclic lower alkyleneimino or 1-oxo-alkyleneimino;
b. each of $R_1$ and $R_2$ is lower alkyl, Ph has the meaning given under (a) and

is 5 to 7 ring-membered, monocyclic 1-oxo-alkyleneimino;
c. each of $R_1$ and $R_2$ is hydrogen or lower alkyl, Ph has the meaning given under (a) and

is 5 to 7 ring-membered, monocyclic lower 2- or 3-alkenyleneimino or 1-oxo-2- or 3
d. $R_1$, $R_2$ and Ph have the meaning given under (a) and

is 5 or 6 ring-membered, bicyclic lower alkenyleneimino with 1–3 double bonds in the ring not containing the imino-nitrogen;
e. $R_1$, $R_2$ and Ph have the meaning given under (b) and

is 5 or 6 ring-membered, bicyclic lower 1-oxo-alkenyleneimino with 1–3 double bonds in the ring not containing the imino-nitrogen; as well as a lower alkyl ester, (lower alkoxy, di-lower alkylamino or lower alkyleneimino)-lower alkyl ester or a therapeutically useful ammonium, alkali metal, alkaline earth metal, aluminum or acid addition salt, of the compounds listed under (a) to (e).

Particularly useful are the compounds of Formula I, wherein:

f. $R_1$ is hydrogen, $R_2$ is hydrogen or alkyl with up to 4 carbon atoms Ph is unsubstituted 1,3- or 1,4-phenylene or such phenylene substituted by one methyl, methoxy, fluoro, chloro, bromo, trifluoromethyl or nitro, and

is pyrrolidino, piperidino, 1,4, 1,5-, 1,6- or 2,5-hexyleneimino;
g. each of $R_1$ and $R_2$ is alkyl with up to 4 carbon atoms, Ph has the meaning given under (f) and

is 2-oxo-(pyrrolidino, piperidino, 1,4-, 1,5- or 1,6-hexyleneimino);
h. each of $R_1$ and $R_2$ is hydrogen or alkyl with up to 4 carbon atoms, Ph has the meaning given under (f) and

is unsubstituted 3-pyrrolino, 3-piperideino, 1,4-pent-2-enyleneimino, 2,5- or 1,6-hex-3-enyleneimino or the 2-oxo- derivative of said groups containing $CH_2$ adjacent to the imino-nitrogen;
i. $R_1$, $R_2$ and Ph have the meaning given under (f) and

is unsubstituted 4,5,6,7-tetrahydroindolino or -isoindolino, 4,7-dihydroindolino or -isoindolino, indolino, isoindolino, 1,2,3,4,5,6,7,8-octahydro-, 1,2,3,4,5,8-hexahydro- or 1,2,3,4-tetrahydroquinolino or -isoquinolino;

j. $R_1$, $R_2$ and Ph have the meaning given under (g) and

is 4,5,6,7-tetrahydroindolino or -isoindolino, 4,7-dihydroindolino or -isoindolino, indolino, isoindolino, 1,2,3,4,5,6,7,8-octahydro-, 1,2,3,4,5,8-hexahydro- or 1,2,3,4-tetrahydroquinolino or -isoquinolino substituted by one oxo group at the carbon atom adjacent to the imino-nitrogen; as well as a lower alkyl ester, the ammonium, sodium, potassium or therapeutically useful acid addition salt of the compound listed under (f) to (j).

Outstanding are the compounds of Formulae II and III

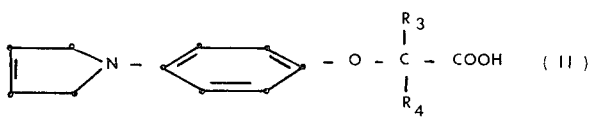

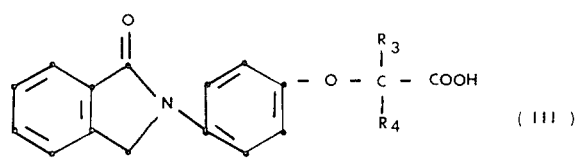

wherein:

k. $R_3$ is hydrogen and $R_4$ is hydrogen, methyl or ethyl or l. $R_3$ is methyl and $R_4$ is methyl or ethyl; or the methyl or ethyl ester or the ammonium, sodium, potassium or therapeutically useful acid addition salt of the compounds listed under (k) and (l), which exhibit in the above described test systems at oral doses between about 1 and 50 mg/kg/day a high order of antiinflammatory, hypocholesterolemic and hypolipidemic activity.

The compounds of the invention are prepared according to methods known per se. For example, they are obtained by a. condensing compounds of the formulae

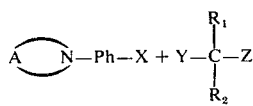

wherein one of X and Y is a free or salified hydroxy group and the other a free or reactively esterified hydroxy group and Z is a free or functionally converted carboxy group or b. ring-closing a compound of the formula

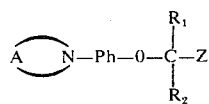

wherein W is amino or a free or reactively etherified or esterified hydroxy group, by eliminating WH and c. converting any resulting compound of the formula $$A\underset{}{\underbrace{\phantom{XX}N}}-Ph-O-\underset{R_2}{\overset{R_1}{C}}-Z$$

wherein Z is different from free, or correspondingly esterified or salified carboxy, into the compounds of the invention.

The condensation according to (a) is advantageously carried out with the use of the corresponding alkali metal phenolates and corresponding alkanoic acid esters or salts, substituted in α-position by a halogen atom or an aliphatic or aromatic acyloxy group e.g., lower alkanoyloxy, alkanesulfonyloxy, benzoyloxy or benzenesulfonyloxy, e.g., acetoxy, benzoyloxy, methane-, ethane-, benzene- or p-toluenesulfonyloxy group. Moreover, said α-halogenated alkanoic acid esters or salts can be obtained intermediarily from corresponding alkanals or alkanones and a haloform under the basic condensing conditions. Corresponding basic condensing agents are advantageously alkali metal hydroxides, carbonates, amides, hydrides, lower alkoxides or tertiary nitrogen bases, such as tri-lower alkylamines, pyridines or quinolines. In case both X and Y represent hydroxy, a strong dehydrating agent is used for the condensation, such as a mineral acid, e.g., sulfuric or polyphosphoric acid, or an aliphatic or aromatic carbonic acid diester or diimide, e.g., dimethyl, diethyl or diphenyl carbonate or dicyclohexyl-carbodiimide. The condensation with alkanones and haloforms, e.g., chloroform or bromoform, is advantageously performed in the presence of alkali metal hydroxides.

The ring-closure according to (b) is preferably performed in situ, i.e., said starting material is obtained by reacting the N-unsubstituted aniline with a compound of the formula V—A—W, wherein one or both of V and W is reactively esterified hydroxy, preferably the halogen or acyloxy listed above for X and the other is also amino, free or etherified hydroxy, e.g., lower alkoxy. Moreover, said starting material is formed in the reduction of corresponding Schiff's bases, i.e., compounds containing a W—A=N— moiety attached to Ph, with complex light metal hydrides, e.g. sodium borohydride. The ring-closing condensing agent is analogous to that used under (a), i.e., it depends on the character of WH to be eliminated. It is one of the bases listed above if WH is an acid, it is one of said acids if WH is an alcohol or base, e.g., an alkanol or ammonia, or it is a dehydrating agent if WH is water.

Any resulting compounds shown under (c) wherein Z is an acylated or amidated carboxy group, e.g., a trichloro or bromomethyl, halocarbonyl, simple or mixed anhydrido, ortho ester, unsubstituted or alkylated carbamoyl,

N-hydroxy or amino-carbamoyl, or cyano group, or the corresponding thio-derivatives thereof, are hydrolyzed and/or desulfurized to the acids of Formula I or their salts according to known methods, for example with aqueous acids or bases, e.g., those mentioned above, if necessary in the presence of desulfurization agents, e.g., zinc, cadmium or lead salts.

The compounds of the invention so obtained can be converted into each other according to methods known per se. For example, resulting free acids may be esterified with the corresponding alcohols in the presence of a strong acid, e.g., hydrochloric, sulfuric, benzene or p-toluene sulfonic acid, or with diazo compounds, or via their halides by pretreatment with thionyl halides or phosphorus halides or oxyhalides. Resulting esters may be hydrolyzed or transesterified in the presence of acidic or alkaline agents, e.g., mineral or complex heavy metal acids or alkali metal carbonates or alcoholates. Resulting compounds which do not contain an oxo group in the bicyclic

moiety can be oxidized therein already with oxygen or other mild oxidation agents, e.g., those mentioned, above, to introduce an oxo group into the A-radical thereof. Any resulting ester or salt containing in α-position at least one hydrogen atom, can be metallized therein, e.g., with the use of alkali metals or their derivatives, such as phenyl lithium, triphenylmethylsodium or sodium hydride, amides or alcoholates, and thereupon reacted with reactive esters of $R_1$—OH and/or $R_2$—OH. Resulting compounds may also be halogenated in the Ph-moiety, e.g., with the use of halogens, which are advantageously applied in the presence of Lewis acids, e.g., ferric, aluminum, antimony III or tin IV halides, or with the use of halogenation agents, e.g., hydrochloric acid and hydrogen peroxide or sodium chlorate, nitrosyl chloride or bromide, bromosuccin- or phthalimide. Furthermore, nitration may be applied to final products, advantageously with the use of nitric acid or nitrates under acidic conditions, e.g., in the presence of sulfuric or trifluoroacetic acid respectively. Resulting nitro compounds may be reduced, for example, with catalytically activated or nascent hydrogen and the primary amines obtained are treated with nitrous acid, to yield diazonium salts, which can be converted according to the Sandmeyer reaction to corresponding hydroxy, halogeno or alkoxy compounds, e.g., by hydrolyzing the diazonium salt at elevated temperatures, or reacting it with cuprous halides or with a lower alkanol respectively, preferably under neutral or slightly acidic or alkaline conditions. In resulting phenolic products, the hydroxy group can be etherified, e.g., by reacting the corresponding alkali metal phenolates with lower alkyl halides or sulfonates. In the above reductions, care should be taken or starting materials and final products properly selected, in order to retain unsaturation in

A resulting acid can be converted into its salts according to conventional methods, for example, by reacting it with an about stoichiometric amount of a suitable salt-forming reagent, such as ammonia or an alkali or alkaline earth metal hydroxide, carbonate or hydrogen carbonate. A salt of this type can be reconverted into the free acid by treatment with an acid, e.g., hydrochloric, sulfuric or acetic acid, until the proper pH has bee reached. A resulting basic compound can be converted into a corresponding acid addition salt, for example by reacting it with an inorganic or organic acid, such as a therapeutically useful acid, or with a corresponding anion exchange preparation, and isolating the desired salt. An acid addition salt may be converted into the free compound by treatment with a base, e.g., a metal hydroxide, ammonia or a hydroxyl ion exchange preparation. Therapeutically useful acids are, for example, inorganic acids, e.g., hydrochloric, hydrobromic, sulfuric, phosphoric, nitric or perchloric acid, or organic acids, e.g., carboxylic or sulfonic acids, such as formic, acetic, propionic, succinic, glycellic lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicylic, embonic, nicotinic, methanesulfonic, ethanesulfonic, hydroxy-ethanesulfonic ethylenesulfonic, benzenesulfonic halogenbenzenesulfonic, toluenesulfonic, naphthalenesulfonic or sulfanilic acid; methionine, tryptophan, lysine or arginine.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this contest, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example by separation of diastereomeric salts thereof, e.g., by the fractional crystallization of d- or l-tartrates or d-α-(1-naphthyl)-ethylamine or 1-cinchonidine salts.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. In the process of the invention, those starting materials are advantageously selected, which yield the above-described preferred embodiments of the invention, especially those corresponding to Formula II or III.

The starting material used is known or, if new, may be prepared according to the methods described for known analogs thereof. For example, the phenols mentioned under item a) can be prepared analogous to the process mentioned under item b), i.e., by introduction or construction of the cyclic amino group

A⌒N— into corresponding phenols or anisols, which latter are hydrolyzed with either pyridinium chloride or hydrobromic acid. The preparation of the compounds shown under item (b) has been mentioned above and the initial α-(prim.aminophenoxy)-alkanoic acids are described in U.S. Pat. No. 3,465,002.

The pharmacologically active compounds of the invention are useful in the manufacture of pharmaceutical compositions containing an effective amount thereof in conjunction or admixture with excipients suitable for either enteral, parenteral or topical application. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories or ointments are advantageously fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50% of the active ingredient.

The following examples are intended to illustrate the invention and are not to be construed as being limitations thereon. Temperatures are given in degrees centigrade, and all parts wherever given are parts by weight.

EXAMPLE 1

To the solution of 10 g of 4-piperidinophenol in 450 ml of dimethylformamide-toluene(1:1), 3 g of a 50% suspension of sodium hydride in mineral oil is added while stirring. After one hour 10.4 g of ethyl bromoacetate are added dropwise and the mixture stirred at room temperature for 1.5 hours. Thereupon 25 ml of water are added dropwise while cooling and the mixture is evaporated under reduced pressure. The residue is taken up in water, the mixture extracted with diethyl ether, the extract dried, filtered and gassed with hydrogen chloride. The precipitate formed is filtered off and recrystallized from acetone, to yield the ethyl (4-piperidinophenoxy)-acetate hydrochloride of the formula

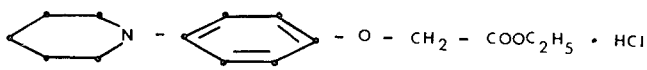

melting at 139°–142°.

EXAMPLE 2

To the solution of 10 g of 4-piperidinophenol in 500 ml of dimethylformamide-toluene(1:1), 3 g of a 50% suspension of sodium hydride in mineral oil is added while stirring. Afer 1 hour 11.2 g of ethyl α-bromopropionate are added dropwise and the mixture stirred at room temperature for two days. Thereupon 25 ml of water are added dropwise while cooling and the mixture is evaporated under reduced pressure The residue is taken up in water, the mixture extracted with diethyl ether, the extract dried, filtered and gassed with hydrogen chloride. The precipitate formed is filtered off and recrystallized from ethanol-diethyl ether, to yield the ethyl α-(4-piperidinophenoxy)-propionate hydrochloride melting at 133°–136°.

EXAMPLE 3

To the solution of 10 g of 4-piperidinophenol in 500 ml of dimethylformamide-toluene(1:1), 3 g of a 50% suspension of sodium hydride in mineral oil is added while stirring. After 1 hour 13 g of ethyl α-bromo-α-methylbutyrate are added dropwise and the mixture stirred at room temperature for 3 days. Thereupon 25 ml of water added dropwise while cooling and the mixture is evaporated under reduced pressure. The residue is taken up in water, the mixture extracted with diethyl ether, the extract dried, filtered and gassed with hydrogen chloride. The precipitate formed is filtered off and recrystallized from ethanol-diethyl ether, to yield the ethyl α-methyl-α(4-piperidinophenoxy)-butyrate hydrochloride melting at 113°–116°.

EXAMPLE 4

The mixture of 8.7 g of ethyl (4-aminophenoxy)-acetate, 12 g of cis-1,4-dibromo-2-butene, 20 g of sodium carbonate and 500 ml of dimethylformamide is refluxed for 1 hour while stirring and allowed to stand at room temperature overnight. It is filtered, the filtrate evaporated under reduced pressure and the residue taken up in water. The mixture is extracted with diethyl ether and ethyl acetate, the combined extract washed with saturated aqueous sodium chloride, dried and evaporated. The residue is recrystallized from ethyl acetate-hexane, to yield the ethyl (4-pyrrolinophenoxy)-acetate of the formula

melting at 102°–104°.

EXAMPLE 5

The mixture of 2 g of ethyl (4-pyrrolinophenoxy)-acetate, 50 ml of 25% aqueous sodium hydroxide and 50 ml of ethanol is refluxed for 8 hours under nitrogen. After cooling it is acidified with 6N hydrochloric acid while cooling to a pH = 5.5 and extracted with diethyl ether. The extract is dried, evaporated and the residue recrystallized from benzene, to yield the (4-pyrrolinophenoxy)-acetic acid melting at 146°–150°.

EXAMPLE 6

The mixture of 5.6 g of ethyl α-(4-aminophenoxy)-isobutyrate, 7.8 g of cis-1,4-dichloro-2-butene, 10.6 g of sodium carbonate and 200 ml of dimethylformamide is stirred at room temperature for 60 hours. It is filtered, the filtrate evaporated under reduced pressure and the residue distilled. The fraction boiling at 145°–150/0.15 mm Hg is collected, to yield the ethyl α-(4-pyrrolinophenoxy)-isobutyrate melting at 48°–50°.

EXAMPLE 7

The mixture of 2.5 g of ethyl α-(4-pyrrolinophenoxy)-isobutyrate, 0.54 g of potassium hydroxide, 0.7 ml of water and 150 ml of ethanol is refluxed while stirring under nitrogen for 5 hours and overnight at room temperature. It is evaporated, the residue taken up in water and the solution washed with diethyl ether. The pH of the aqueous solution is adjusted with 6N hydrochloric acid to 4 while cooling, followed by extraction with diethyl ether. The extract is dried and evaporated, to yield the α-(4-pyrrolinophenoxy)-isobutyric acid melting at 122°–124°.

EXAMPLE 8

The mixture of 4.3 g of ethyl α-[4-(2-carboxy-benzylideneimino)-phenoxy]-isobutyrate, 0.9 g of sodium borohydride and 200 ml of ethanol is refluxed for two hours and stirred oernight at room temperature. It is diluted with 10 ml of water, the pH thereof adjusted to 4 with 6N hydrochloric acid and extracted wth ethyl acetate. The extract is dried, filtered, evaporated and the residue recrystallized from diethyl ether, to yield the ethyl α-[4-(1-oxoisoindolino)-phenoxy]-isobutyrate of the formula

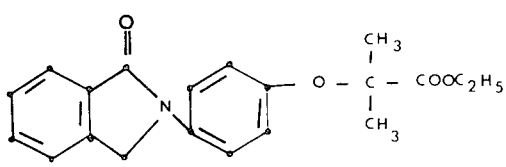

melting at 86°–88°.

The starting material is prepared as follows: The mixture of 4 g of ethyl α-(4-aminophenoxy)-isobutyrate, 2.7 g of 2-formylbenzoic acid, 200 ml of toluene and few crystals of p-toluenesulfonic acid is refluxed overnight on a water trap. After collection of the theoretical amount of water it is evaporated under reduced pressure and the residue recrystallized from ethanol, to yield the ethyl α-[4-(2-carboxybenzylideneimino)-phenoxy]-isobutyrate, melting at 130°–133°.

EXAMPLE 9

Preparation of 1000 tablets, each containing 50 mg of the active ingredient:
Formula:

| | |
|---|---|
| α-(4-pyrrolinophenoxy)-isobutyric acid | 33.0 g |
| Lactose U.S.P. | 51.7 g |
| Corn starch | 13.0 g |
| Stearic Acid | 1.0 g |
| Magnesium Stearate | 1.0 g |
| Colloidal Silica | 0.3 g |
| Purified water | q.s. |

Procedure:

All the powders are passed separately through a screen with 0.3 mm openings and mixed well. From one-third of the starch and a suitable amount of water, a paste is formed in order to granulate the powders of the active ingredient, the lactose and one-third of the starch, if necessary, with an additional amount of water. The granulate is dried overnight at 35°, broken on a screen with 1.2 mm openings, mixed with the remainder of the starch, the stearic acid, magnesium stearate and colloidal silica, and compressed into 150 mg tablets using concave punches with 7.1 mm diameter, uppers bisected.

In the analogous manner tablets are prepared, each containing 50 mg of the other compounds of the invention, advantageously those illustrated by the examples herein.

EXAMPLE 10

Preparation of 10,000 capsules each containing 100 mg of the active ingredients:
Formula:

| | |
|---|---|
| ethyl α-(4-piperidinophenoxy)-propionate hydrochloride | 1,000.0 g |
| Lactose | 2,800.0 g |
| Talcum powder | 200.0 g |

Procedure:

All the powders are passed through a screen with openings of 0.6 mm. Then the drug substance is placed in a suitable mixer and mixed first with the talcum, then with the lactose until homogeneous. No. 1 hard-gelatin capsules are filled with 400 mg each, using a capsule filling machine.

In the analogous manner capsules are prepared, each containing 100 mg of the other compounds of the invention, advantageously those illustrated by the examples herein.

EXAMPLE 11

According to the methods illustrated by the previous examples, the following compounds of the invention are prepared:

a. α-[3- or 4-(pyrrolidino-; piperidino-; 1,4-, 1,5-, 1,6- or 2,5-hexyleneimino)-phenoxy]-propionic or -isobutyric acid;

b. the 3-(methyl, methoxy, fluoro, chloro, bromo, trifluoromethyl or nitro)-phenoxy derivative of the acids mentioned under items (a) and c. the methyl, ethyl, n- or i-propyl or -butyl ester, the ammonium, sodium, potassium or addition salt of the acids listed in paragraph 14 of the section titled Description of the Preferred Embodiments and the compounds mentioned under items (a) and (b).

I claim:

1. A compound of the formula $$A \quad N-Ph-O-\underset{R_2}{\overset{R_1}{\underset{|}{C}}}-COOH$$

in which each of $R_1$ and $R_2$ is hydrogen or lower alkyl, pH is unsubstituted phenylene or phenylene substituted by one or two members of the group consisting of lower alkyl, lower alkoxy, halogeno, trifluoromethyl or nitro and $$A\!\!\frown\!\!N$$

is 5 to 7-ring-membered lower alkyleneimino or a lower alkyl ester, (lower alkoxy, di-lower alkylamino or lower alkyleneimino)-lower alkyl ester or a therapeutically useful ammonium, alkali metal, alkaline earth metal, aluminum or acid addition salt thereof.

2. A compound as claimed in claim 1, in which formula each of R and $R_2$ is hydrogen or lower alkyl, pH is 1,3- or 1,4-phenylene, (lower alkyl)-1,3- or 1,4-phenylene, (lower alkoxy)-1,3-or 1,4-phenylene, mono- or di- (halogeno)-1,3- or 1,4-phenylene, (trifluoromethyl)-1,3- or 1,4-phenylene or (nitro)-1,3- or 1,4-phenylene and $$A\!\!\frown\!\!N$$

is 5 to 7 ring-membered lower alkyleneimino or a lower alkyl ester, (lower alkoxy, di-lower alkylamino or lower alkyleneimino)-lower alkyl ester or a therapeutically useful ammonium, alkali metal, alkaline earth metal, aluminum or acid addition salt thereof.

3. A compound as claimed in claim 1, in which formula $R_1$ is hydrogen, $R_2$ is hydrogen or lower alkyl, pH is 1,3- or 1,4-phenylene, (lower alkyl)-1,3- or 1,4-phenylene, (lower alkoxy)-1,3-or 1,4-phenylene, mono-di(halogeno)-1,3- or 1,4-phenylene, (trifluoromethyl)-1,3- or 1,4-phenylene or (nitro)-1,3- or 1,4-phenylene, and $$A\!\!\frown\!\!N$$

is 5 to 7 ring-membered lower alkyleneimino, or a lower alkyl ester, (lower alkoxy, di-lower alkylamino or lower alkyleneimino)-lower alkyl ester or a therapeutically useful ammonium, alkali metal, alkaline earth metal, aluminum or acid addition salt thereof.

4. A compound as claimed in claim 1, in which formula $R_1$ is hydrogen, $R_2$ is hydrogen or alkyl with up to 4 carbon atoms, Ph is unsubstituted 1,4-phenylene or such phenylene substituted by one methyl, methoxy, fluoro, chloro, bromo, trifluoromethyl or nitro and $$A\!\!\frown\!\!N$$

is pyrrolidino, piperidino, 1,4-, 1,5-, 1,6- or 2,5-hexyleneimino, or a lower alkyl ester, the ammonium, sodium or therapeutically useful acid additional salt thereof.

5. A compound as claimed in claim 1 and being the α-[3- or 4-(pyrrolidino-; piperidino-; 1,4-, 1,5-, 1,6- or 2,5-hexyleneimino)-phenoxy]-propionic or -isobutyric acid, or the methyl, ethyl, n- or i-propyl or -butyl ester, the ammonium, sodium, potassium or therapeutically useful acid addition salt thereof.

6. A compound as claimed in claim 1 and being the ethyl (4-piperidinophenoxy)-acetate hydrochloride.

7. A compound as claimed in claim 1 and being the ethyl α-(4-piperidinophenoxy)-propionate hydrochloride.

8. A compound as claimed in claim 1 and being the ethyl α-methyl-α-(4-piperidinophenoxy)-butyrate hydrochloride.

* * * * *